United States Patent
Krueger et al.

(10) Patent No.: US 9,471,850 B2
(45) Date of Patent: Oct. 18, 2016

(54) REGISTERING METHOD, POSITION DETECTING SYSTEM, AND SCANNING INSTRUMENT

(71) Applicant: FIAGON GMBH, Hennigsdorf (DE)

(72) Inventors: Timo Krueger, Berlin (DE); Dirk Mucha, Berlin (DE)

(73) Assignee: FIAGON GMBH, Hennigsdorf (DE)

( * ) Notice: Subject to any disclaimer, the term of this patent is extended or adjusted under 35 U.S.C. 154(b) by 0 days.

(21) Appl. No.: 14/358,108

(22) PCT Filed: Nov. 15, 2012

(86) PCT No.: PCT/EP2012/072783
§ 371 (c)(1),
(2) Date: May 14, 2014

(87) PCT Pub. No.: WO2013/072434
PCT Pub. Date: May 23, 2013

(65) Prior Publication Data
US 2014/0314297 A1    Oct. 23, 2014

(30) Foreign Application Priority Data

Nov. 15, 2011   (DE) .................. 10 2011 119 073

(51) Int. Cl.
*G06K 9/62* (2006.01)

(52) U.S. Cl.
CPC ............. *G06K 9/6267* (2013.01); *A61B 34/20* (2016.02); *A61B 2034/2051* (2016.02); *A61B 2034/2068* (2016.02); *A61B 2034/2072* (2016.02)

(58) Field of Classification Search
None
See application file for complete search history.

(56) References Cited

U.S. PATENT DOCUMENTS

| 6,011,987 | A | 1/2000 | Barnett |
| 7,491,198 | B2 | 2/2009 | Kockro |
| 2003/0231793 | A1 | 12/2003 | Crampton |
| 2004/0019274 | A1 | 1/2004 | Galloway, Jr. et al. |
| 2005/0101966 | A1 | 5/2005 | Lavallee |
| 2005/0149050 | A1* | 7/2005 | Stifter et al. .................. 606/102 |
| 2008/0255442 | A1 | 10/2008 | Ashby et al. |
| 2008/0319448 | A1 | 12/2008 | Lavallee et al. |
| 2010/0307516 | A1 | 12/2010 | Neubauer et al. |

FOREIGN PATENT DOCUMENTS

| DE | 19641720 | 4/1998 |
| EP | 1523951 | 4/2005 |
| WO | WO 2007/011314 | 1/2007 |
| WO | WO 2011/134083 | 11/2011 |

OTHER PUBLICATIONS

International Search Report and Written Opinion for International (PCT) Patent Application No. PCT/EP2012/072783 mailed Feb. 13, 2013, 9 pages.

Official Action (No English translation available) for German Patent Application No. 102011119073.6 dated Jun. 20, 2012, 6 pages.

* cited by examiner

*Primary Examiner* — Soo Park
(74) *Attorney, Agent, or Firm* — Sheridan Ross P.C.

(57) ABSTRACT

The invention relates to a method for assigning position values, detected by means of a position detection system, to a topographic image of an object or body part, which comprises the following steps:
providing a topographic model of an object or body part,
scanning a surface of the object or body,
detecting position values during the scanning and
assigning detected position values to corresponding positions in the topographic model, the detected position values being assigned to points of a virtual surface of the topographic model, which has a distance from a model surface which corresponds to a radius of a partly spherical scanning tip of a scanning instrument, by means of which the surface of the object or body part is scanned in each case.

9 Claims, 2 Drawing Sheets

REGISTERING METHOD, POSITION DETECTING SYSTEM, AND SCANNING INSTRUMENT

CROSS REFERENCE TO RELATED APPLICATIONS

Figure 1:
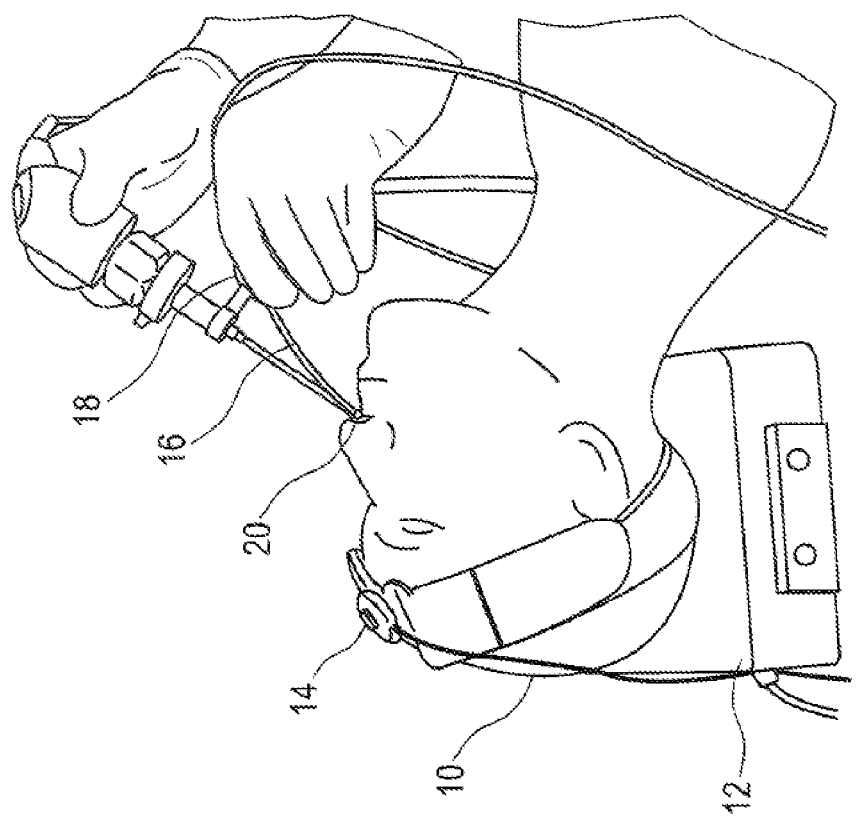

This application is a national stage application under 35 U.S.C. 371 and claims the benefit of PCT Application No. PCT/EP2012/072783 having an international filing date of Nov. 15, 2012, which designated the United States, which PCT application claimed the benefit of German Application No. 102011119073.6 filed Nov. 15, 2011, the disclosure of both the above-identified applications are incorporated herein by reference.

The invention relates to a method for assigning position values, detected by means of a position detection system, to a topographic image of an object or body part. Moreover, the invention relates to a position detection system comprising a movable scanning instrument, and a scanning instrument itself.

In principle, position detection systems which, for example in the medical sector, assist a navigation of instruments, e.g. surgical instruments, are known. Such position detection systems can be optical, ultrasound-based or electromagnetic position detection systems. Thus, for example, electromagnetic position detection systems are known, in which a field generator produces an alternating electromagnetic field and position sensors having coils are provided. The alternating electromagnetic field of the generator induces currents in the coils, which currents depend on the alignment of a respective coil with respect to the alternating electromagnetic field. If a movable instrument with such position sensors in the form of sensor coils is aligned, it is possible to determine position and alignment of the instrument relative to a reference sensor which, for example, may likewise have coils. Here, the reference sensor, as patient localizer, is preferably securely connected to a body part of a patient (or else a different object).

For the purposes of navigation in body parts of a patient, the position of an instrument is typically detected by means of such a position detection system and the position of the instrument is displayed in tomographically obtained slice images of the body part. In order for this to work, the position values, which are supplied by the position sensor of the instrument, need to be transformed into coordinates of the tomographic image of the patient. By way of example, in this respect, it is known to generate a topographic image of the surface of a body part from a tomographic image of a patient in order to assign points on the surface of the topographic image (also referred to as model surface in the following text) to such points on the surface of the real body part, which are in each case contacted by a pointer or scanning instrument; thus it is possible, within the scope of a registration method, to establish a transformation prescription for position values, detected by means of the position detection system, into model coordinates. To this end, a plurality of points are scanned on the real surface of the body part and the associated position values, which of course represent points on a real surface, are, while maintaining their relative position with respect to one another, assigned to points on the model surface in such a way that this results in an error which is as small as possible. What emerges from this is a transformation prescription specifying how detected position values are to be converted into coordinates of the topographic image—also referred to here as topographic model—and therefore also into coordinates of the tomographic image or model.

The invention is based on the object of developing such a method known per se, a position detection system and a scanning instrument.

According to the invention, this object is achieved, firstly, by a method of the type set forth at the outset, which comprises the following steps:
 providing a topographic model of an object or body part,
 scanning a surface of the object or body part,
 detecting position values during the scanning and
 assigning detected position values to corresponding positions in the topographic model, the detected position values being assigned to points of a virtual surface of the topographic model, which has a distance from a model surface which corresponds to a radius of a partly spherical scanning tip of a scanning instrument, by means of which the surface of the object or body part is scanned in each case.

As position detection system, use is preferably made of a position detection system comprising a movable scanning instrument having a scanning tip with a sphere-shaped external surface and having a sphere center as position reference point. For assigning position values, detected by means of the scanning instrument, to individual points, a virtual model surface is determined proceeding from a model surface defined by the topographic model, which model surface has a distance, equaling the distance of the sphere center of the scanning tip from the sphere-shaped external surface thereof, from the model surface. What is meant by a movable scanning instrument is an instrument which is movable relative to the body part or object to be scanned, in contrast, for example, to a position sensor secured to an object or body part.

Such a method allows the use scanning instruments, the scanning tip of which is not pointed in the proper meaning of the word, but rather has a sphere-shaped surface, i.e. a surface corresponding to a partial sphere. The diameter of the partly spherical scanning tip can in this case be selected to be comparatively large, for example larger than a shank of the scanning instrument, which shank connects the scanning tip to a handle. Such a scanning instrument with a scanning tip with a relatively large sphere radius can be guided more easily and more gently over a soft surface, as can be found e.g. in parts of the face of a patient.

The disadvantage of such a scanning instrument with a spherical scanning tip is that the position detection system cannot detect with what point of the sphere surface the scanning instrument is contacting the respective surface at a particular time. By way of example this point can lie precisely along an extension of a longitudinal axis of a shank connecting the scanning tip to a handle if the scanning instrument is placed precisely perpendicularly onto the surface. However, if the scanning instrument is placed onto the surface at an angle, a different point of the spherical scanning tip contacts the surface of the body part, and this would result in a positional error which can easily be a few millimeters and, as such, cannot be repaired. In order to compensate this error, virtual surfaces are, according to the invention, calculated from the surfaces of the tomographic model or topographic model, which virtual surfaces have a distance from the actual model surfaces, which corresponds precisely to the radius of the partly spherical scanning tip of the scanning instrument. Then, the center of the partly spherical tip of the scanning instrument can be used as position reference point of the scanning instrument, the relative position of which center point both from the model surface and from the virtual model surface being independent of the angle at which the instrument is placed onto the respective surface of the body part or object.

Within the scope of the registration method according to the invention, detected position values, which are related to the sphere center of the partly spherical scanning tip as position reference point, are assigned to positions on the virtual model surface in such a way that, while maintaining the relative position of the detected position values with respect to one another and applying a uniform transformation prescription for all position values, a correspondence with the best possible fit emerges between the detected position values and positions on the virtual model surface.

According to the invention, the object is also achieved by a position detection system comprising a movable scanning instrument, the movable scanning instrument having a scanning tip with a sphere-shaped, i.e. partly spherical external surface, with the sphere center of the spherical scanning tip serving as position reference point. The position detection system furthermore comprises a storage medium for a topographic model of an object or body part and, according to the invention, is embodied to transfer position values detected by a movable instrument into a model coordinate system, underlying the topographic model, by means of a transformation prescription. The position detection system is furthermore embodied to carry out an assignment of position values detected by means of the scanning instrument with partly spherical scanning tip to points or positions on a model surface defined by the topographic model by virtue of the position detection system assigning position values relating to the sphere center of the scanning tip as a position reference point to a virtual surface which has a distance, which corresponds precisely to the sphere radius of the partly spherical scanning tip, from a model surface defined by the topographic model.

For registration purposes, the position detection system can additionally be embodied to establish a transformation prescription for converting detected position values into model coordinates, the transformation prescription having the property of resulting in an overall deviation, which is a small as possible, of detected position values from assigned points on the virtual model surface during the assignment of position values detected within the scope of a registration to points or positions on the virtual model surface.

According to the invention, the underlying object is also achieved by a scanning instrument having a partly spherical scanning tip which preferably has a diameter of more than 3 mm. In accordance with a preferred embodiment variant, the partly spherical scanning tip can be formed by a sphere which is rotatable in the manner of a ballpoint pen tip. The scanning tip can also be embodied to emit a lubricant gel or the like such that it is easier for the scanning tip to slide over a surface to be scanned.

Figure 2:
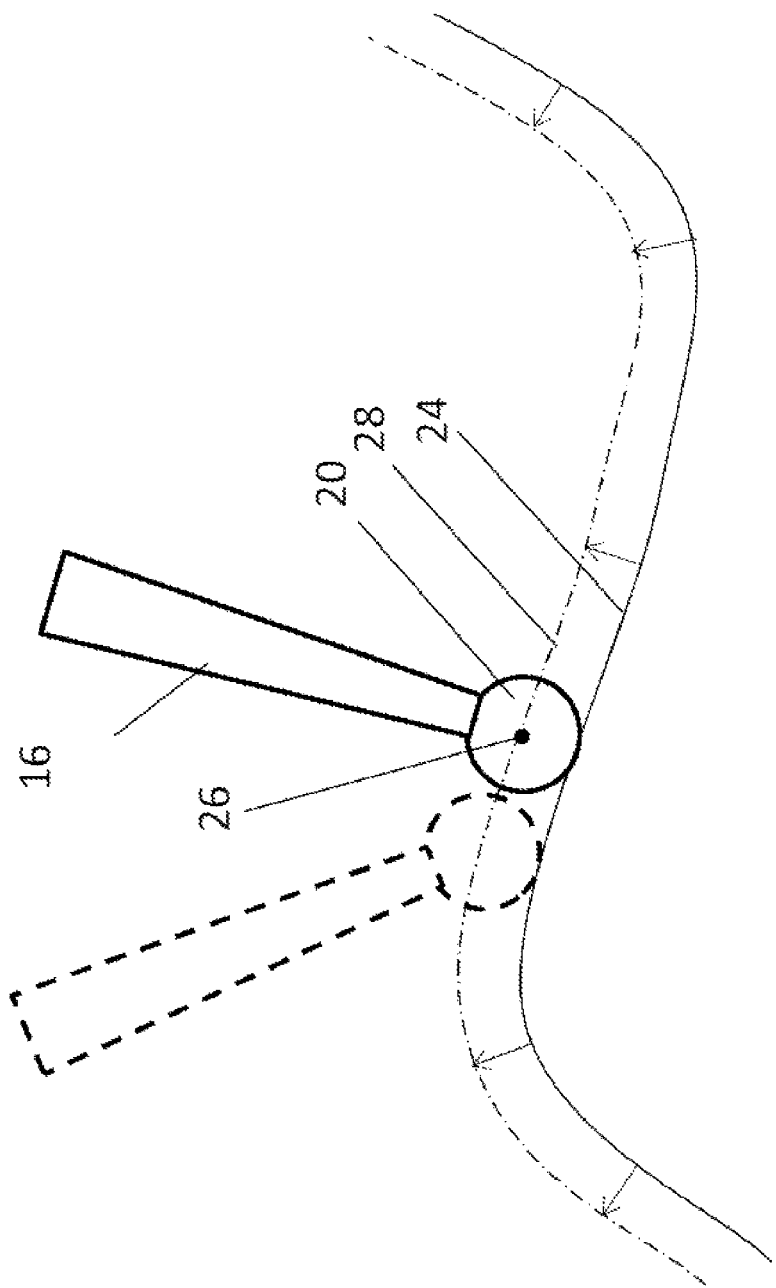

Now, with reference to the figures, the invention is intended to be explained in more detail on the basis of an exemplary embodiment. In detail:

FIG. 1 shows a position detection system according to the invention, comprising a field generator for an alternating electromagnetic field, a position sensor (patient localizer) secured to the patient and a movable scanning instrument; and FIG. 2 shows a sketch of a distal end of a scanning instrument according to the invention, comprising a partly spherical scanning tip and an indicated virtual surface for explaining the principle underlying the invention.

FIG. 1 shows, by way of a sketch, a head 10 of a patient in a side view. Situated in the vicinity of the head 10, there is a field generator 12 for generating an alternating electromagnetic field, which can be detected in the region of the head of the patient. Attached to the head 10 of the patient, there is a position sensor secured to the patient as a reference position sensor 14 or as patient localizer. A movable scanning instrument 16 has a proximal end with a handle 18 and a distal end with a partly spherical scanning tip 20. An instrument position sensor 22 is fastened on, or in, the scanning instrument 16. The reference position sensor 14 and the instrument position sensor 22 each have one or more electrical coils. The alternating electromagnetic field, emanating from the field generator 12 during operation thereof, induces a current in the coils in each case, the amplitude (and phase?) of which current depends on the relative position and alignment of a respective sensor coil with respect to the field generator 12. In this manner it is possible, in a manner known per se, to determine the relative position and alignment of the instrument position sensor in relation to the reference position sensor.

In order to use position values, detected by means of a position detection system, of an instrument for instrument navigation within the meaning that a respectively current position of an instrument is displayed in e.g. tomographically obtained slice images of a body part, it is necessary to transform the position values supplied by the position sensor of the instrument into a model coordinate system underlying a tomographic image. A transformation prescription required for this is obtained in a manner known per se by means of a registration method. To this end, for example, a surface of a body part is scanned by means of a pointer or scanning instrument, and position values obtained in the process are transferred with an error, which is as small as possible, to a model surface derived from a tomographic or topographic image. The scalings, rotations and/or translations or the like, required for this transfer, which is as accurate as possible, ultimately result in the transformation prescription.

FIG. 2 shows a distal end of a scanning instrument 16 with a partly spherical scanning tip 20. The distal end of the scanning instrument 16 is depicted twice in FIG. 2, namely once using a full line and once using dashed lines. The dashed representation indicates that a different point of the partly spherical scanning tip contacts the surface 24 of an object or body part if the scanning instrument 16 is placed onto this surface 24 at a different angle. Since the angle at which a scanning instrument is placed onto the respective surface is generally unknown, a precise determination of the position on the basis of the contact point as a reference point is not possible using a scanning instrument with a partly spherical scanning tip. Thus, according to the invention, the sphere center 26 of the partly spherical scanning tip 20 is used as position reference point of the scanning instrument 16. However, the sphere center 26 has a distance from the surface 24 of the body part or object. As a result, this can result in scanning situations, for example in body grooves, in which the sphere center can no longer be unambiguously assigned to a point on the surface of the body.

In order to circumvent this problem, position values, which are detected by means of the scanning instrument 16 and are related to the sphere center of the scanning tip 20 as position reference point, are not assigned to a point on a model surface as it emerges from a topographic or tomographic image of the respective body part or object. Rather, a virtual model surface 28 is calculated from the respective model surface, which virtual model surface has a distance, which corresponds precisely to the radius of the partly spherical scanning tip, from the model surface. In FIG. 2, this virtual model surface 28 is represented by dash-dotted lines. The virtual model surface is determined by the endpoints of surface normals on the model surface, wherein the length of the surface normal corresponds to the radius of the scanning tip. This is indicated in FIG. 2 by a few arrows which correspond to surface normals. Position values relating to the sphere center of the scanning point as position reference point can be unambiguously assigned to the virtual model surface 28, this being independent of the angle with which the scanning instrument 16 is placed on the surface of the body part or object.

Therefore, it becomes possible for exact positions also to be detected using a scanning instrument which has a scanning tip with a large radius compared to the prior art. A scanning tip with a large radius moreover offers the advantage that such a scanning tip is not as easily caught in body grooves or the like.

LIST OF REFERENCE SIGNS

10 Head
12 Field generator
14 Reference position sensor
16 Scanning instrument
18 Handle
20 Scanning tip
22 Instrument position sensor
24 Surface
26 Sphere center
28 Model surface

The invention claimed is:

1. A method for assigning position values, detected by means of a position detection system, to a topographic image of an object or body part, the method comprising the following steps:
    providing a scanning instrument having a partly spherical scanning tip,
    providing a topographic model of an object or body part having a model surface,
    calculating from the model surface of said topographic model a virtual model surface that has a distance from the model surface, which equals a radius of the partly spherical scanning tip of the scanning instrument,
    scanning a surface of the object or body part by means of said scanning instrument,
    detecting position values that are related to the sphere center of the scanning tip during the scanning, and
    assigning detected position values to points of said virtual surface of the topographic model.

2. A method according to claim 1, characterized by the method step:
    establishing a transformation prescription for transforming position values and/or coordinates of the position detection system to model position values and/or model coordinates of the topographic model, or vice versa.

3. A method according to claim 1, wherein a position detection system comprising a field generator for an alternating electromagnetic field and comprising at least two position sensors, each with at least one electrical coil, is used as position detection system, of which position sensors one position sensor is connected to the object or body part in such a way that this position sensor maintains a fixed relative position in relation to the object or body part, while the other position sensor is fastened to the scanning instrument.

4. A method according to claim 1, wherein the topographic model is recorded by means of a tomographic method.

5. A method according to claim 1, wherein, when assigning the detected position values to corresponding positions in the topographic model, a plurality of position values recorded at different positions of the object or body part are assigned to points on the virtual model surface in such a way that this results in an error which is as small as possible in the case of linear scaling and rotation.

6. A position detection system, comprising:
    a movable scanning instrument, the movable scanning instrument having a scanning tip with a partly spherical external surface and the sphere center of the sphere-shaped scanning tip serving as position reference point; and
    a storage medium for a topographic model of an object or body part and being embodied to transfer position values detected by a movable instrument into a model coordinate system, underlying the topographic model, by means of a transformation prescription in such a way that position values detected by means of the scanning instrument with partly spherical scanning tip are assigned to points or positions on a model surface defined by the topographic model by virtue of the position detection system assigning position values, related to the sphere center of the scanning tip as position reference point, to a virtual surface which has a distance from a model surface defined by the topographic model, which distance corresponds precisely to the sphere radius of the partly spherical scanning tip.

7. A position detection system according to claim 6, wherein the position detection system is furthermore embodied, for establishing the transformation prescription, to carry out an assignment of position values detected by means of the scanning instrument to points on a model surface defined by the topographic model by virtue of the position detection system determining a virtual model surface which has a distance from the model surface which equals the distance of the sphere center of the scanning tip from the sphere-shaped external surface thereof and assigning position values detected by means of the scanning instrument as precisely as possible to the virtual model surface while maintaining the relative position of said position values to one another.

8. The position detection system according to claim 6, wherein the position detection system is a position detection system comprising a field generator for an alternating electromagnetic field and comprising at least two position sensors, each with at least one electrical coil, of which position sensors one position sensor is to be connected to the object or body part in such a way that this position sensor maintains a fixed relative position in relation to the object or body part, while the other position sensor is fastened to the scanning instrument.

9. The position detection system according to claim 6, wherein the scanning instrument has a proximal end with a handle and a distal end with a partly spherical scanning tip, which is connected to the handle via a shank, and the position sensor of the scanning instrument is embodied to supply position values which supply a location and alignment of the scanning instrument in relation to a reference sensor, the position sensor having a known, fixed location from the sphere center of the partly spherical scanning tip and the position detection system being embodied to derive, from position values of the position sensor of the scanning instrument, position values of the sphere center of the partly spherical scanning tip as position reference values of the scanning instrument for assigning position values to points on a model surface defined by the topographic model.

* * * * *